United States Patent [19]

Mathison et al.

[11] 3,954,774
[45] May 4, 1976

[54] N-SUBSTITUTED-7,8-DIHYDROXYCYCLOPENTANO[F]-1,2,3,4-TETRAHYDROISOQUINOLINES AND ETHERS AND ESTERS THEREOF

[75] Inventors: Ian William Mathison; William Ebenezer Solomons, both of Memphis, Tenn.; Raymond Henry Jones, Northport, N.Y.

[73] Assignee: Marion Laboratories, Inc., Kansas City, Mo.

[22] Filed: Mar. 28, 1974

[21] Appl. No.: 455,673

[52] U.S. Cl.............. 260/287 CF; 260/286 R; 260/286 Q; 260/289 C; 260/283.5 Y; 260/570.5 CA; 260/599; 260/645; 260/668 F; 424/258
[51] Int. Cl.$^2$............ C07D 217/18; C07D 217/06; C07D 217/16
[58] Field of Search............ 260/287 R, 289 CF

[56] References Cited
UNITED STATES PATENTS

| | | | |
|---|---|---|---|
| 1,942,108 | 1/1934 | Laska et al.................. | 260/287 R |
| 3,318,896 | 5/1967 | Pribyl et al.................. | 260/289 C |
| 3,567,733 | 3/1971 | Nomine et al................ | 260/287 R |

FOREIGN PATENTS OR APPLICATIONS

| | | | |
|---|---|---|---|
| 1,912,944 | 10/1970 | Germany.................. | 260/287 |

OTHER PUBLICATIONS
Burger, "Medicinal Chemistry," pp. 42, 497.

*Primary Examiner*—Joseph A. Narcavage
*Assistant Examiner*—David E. Wheeler
*Attorney, Agent, or Firm*—Merriam, Marshall, Shapiro & Klose

[57] ABSTRACT

N-substituted cyclopentano[f]-1,2,3,4-tetrahydroisoquinolines of the formula

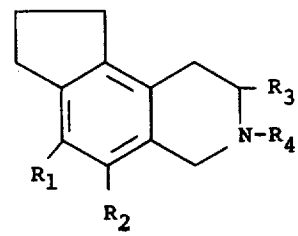

wherein $R_1$ and $R_2$ represent hydroxy, lower alkoxy, lower alkanoyloxy or aryl-lower alkanoyl groups, $R_3$ represents hydrogen or a lower alkyl group and $R_4$ represents a lower alkyl, arylcarbonyl, aryl-lower alkyl, benzhydryl-lower alkyl, lower alkanoyl, aryl-lower alkanoyl, benzhydryl-lower alkanoyl or benzhydrylcarbonyl group, and acid addition salts and quaternary ammonium salts thereof, and pharmaceutical compositions containing one or more of the compounds useful for lowering blood pressure in animals.

22 Claims, No Drawings

N-SUBSTITUTED-7,8-DIHYDROXYCYCLOPEN-TANO[F]-1,2,3,4-TETRAHYDROISOQUINOLINES AND ETHERS AND ESTERS THEREOF

This invention relates to novel chemical compounds and their production. More particularly, this invention provides novel tetrahydroisoqinolines, processes for producing the compounds, and novel pharmaceutical compositions containing the compounds which are useful for effecting desirable pharmacological activity in animals.

According to one aspect of the subject invention there is provided novel N-substituted cyclopentano[f]-1,2,3,4-tetrahydroisoquinolines of Formula 1

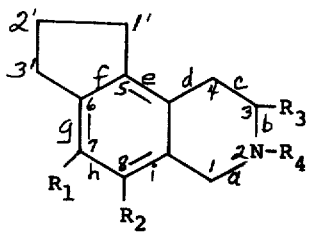

Formula 1 wherein $R_1$ and $R_2$ are hydroxy, lower alkoxy, lower alkanoyloxy or aryl-lower alkanoyloxy groups, $R_3$ is hydrogen or a lower alkyl group, and $R_4$ is a lower alkyl, arylcarbonyl, aryllower alkyl, benzhydryl-lower alkyl, lower alkanoyl, aryllower alkanoyl, benzhydryl-lower alkanoyl or benzhydrylcarbonyl group, and acid addition salts and quaternary ammonium salts of those compounds which form such salts.

The term "lower alkyl" as used herein includes straight or branched chain alkyl groups having 1 to 8, and advisably 1 to 6, carbon atoms such as methyl, ethyl, n-propyl, isopropyl, n-butyl, sec-butyl, n-pentyl, isopentyl and n-hexyl.

The term "aryl" as used herein includes the phenyl group and phenyl groups containing one to three nuclear substituents selected from (1) lower alkoxy groups such as the methoxy and ethoxy groups, (2) lower alkyl groups such as the methyl and ethyl groups, (3) halo groups including the chloro, bromo and fluoro groups, (4) the hydroxy group and (5) the amino group.

The term "benzhydryl" includes the benzhydryl group and benzhydryl groups having, on one or both of the phenyl rings, one to three nuclear substituents selected from (1) lower alkoxy groups such as the methoxy and ethoxy groups, (2) lower alkyl groups such as the methyl and ethyl groups, (3) halo groups including the chloro, bromo and fluoro groups, (4) the hydroxy group and (5) the amino group.

The term "lower alkanoyl" includes saturated, monovalent groups derivable from monocarboxylic acids, including straight and branched chain groups having 1 to 8, and advisably 1 to 6, carbon atoms, such as formyl, acetyl, propionyl, α-methylpropionyl, butyryl and hexanoyl.

The term "lower alkanoyloxy" includes saturated monovalent groups from monocarboxylic acids, including straight and branched groups, having 1 to 8, and advisably 1 to 6, carbon atoms such as the formyloxy, acetoxy, propionyloxy and butyryloxy groups.

The N-substituted -7,8-dialkoxycyclopentano[f]-1,2,3,4-tetrahydroisoquinolines of Formula 2

Formula 2 wherein $R_5$ and $R_6$ are lower alkoxy, and $R_3$ and $R_4$ have the assigned significance but $R_4$ has at least 2 carbons, all of which compounds come within Formula 1, can be produced by reacting a 7,8-di-lower alkoxycyclopentano[f]-1,2,3,4-tetrahydroisoquinoline with an alkanoyl halide, an aryllower alkanoyl halide or a benzhydryl-lower alkanoyl halide to produce an $$R_7-\overset{O}{\underset{\|}{C}}-N-$$

7,8-dialkoxycyclopentano[f]-1,2,3,4-tetrahydroisoquinoline which is then reduced to the $R_4$-N-7,8-dialkoxycyclopentano[f]-1,2,3,4-tetrahydroisoquinoline. This process can be represented as follows:

Formula 3 wherein $R_3$, $R_4$, $R_5$ and $R_6$ have the previously assigned significance, X is a reactive halo group such as the bromo and chloro groups and —$CH_2$-$R_7$ equals $R_4$.

Some of the tetrahydroisoquinolines which can be used as starting materials in the described process are 7,8-dimethoxycyclopentano[f]-1,2,3,4-tetrahydroisoquinoline, 7,8-diethoxycyclopentano[f]-1,2,3,4-tetrahydroisoquinoline, 7,8-dipropoxycyclopentano[f]-1,2,3,4-tetrahydroisoquinoline and 7-methoxy-8-ethoxycyclopentano[f]-1,2,3,4-tetrahydroisoquinoline.

Some alkanoyl halides and aryl-substituted alkanoyl halides which can be used in the first step of the process are acetyl chloride, propionyl chloride, butyryl bromide, benzoyl chloride, p-methoxybenzoyl chloride, 3,4-dimethoxybenzoyl chloride, 3,4,5-trimethoxybenzoyl chloride, diphenylacetyl chloride, diphenylpropionyl bromide, 3,4-dimethoxyphenylacetyl chloride, 4-methylbenzoyl chloride, 4-fluorophenylacetyl chloride and 3,4-diethoxybenzoyl chloride.

Reaction between the tetrahydroisoquinoline and alkanoyl halide, or aryl-substituted alkanoyl halide, to form the desired amide is readily effected by bringing the reactants together in an inert liquid reaction medium, such as benzene or toluene, in the presence of an acid binding agent, such as triethylamine. Heating of the mixture, such as at reflux temperature, increases the reaction rate. After the reaction is terminated the amide reaction product can be isolated from the reaction mixture by conventional procedures.

Representative of the amides which can be produced as described from the appropriate reactants are N-acetyl-7,8-dimethoxycyclopentano[f]-1,2,3,4-tetrahydroisoquinoline, N-propionyl-7,8-diethoxycyclopentano[f]-1,2,3,4-tetrahydroisoquinoline, N-(3,4-dimethoxybenzoyl)-7,8-dimethoxycyclopentano[f]-1,2,3,4-tetrahydroisoquinoline, N-(3,4-dimethoxyphenylacetyl)-7,8-dimethoxycyclopentano[f]-1,2,3,4-tetrahydroisoquinoline, N-(diphenylacetyl)-7,8-dimethoxycyclopentano [f]-1,2,3,4-tetrahydroisoquinoline, N-(4-fluorophenylacetyl)-7,8-dimethoxycyclopentano[f]-1,2,3,4-tetrahydroisoquinoline and N-(3,4,5-trimethoxybenzoyl)-7,8-dimethoxycyclopentano [f]-1,2,3,4-tetrahydroisoquinoline.

The amides can be readily reduced chemically to the tertiary amine compounds of Formula 2 where $R_4$ has at least 2 carbon atoms. Chemical reduction of the amides can be effected by use of a suitable reducing agent, such as lithium aluminum hydride in anhydrous ether, at a temperature which increases the reaction rate, such as the reflux temperature. The resulting tertiary amine can be recovered and isolated as an acid addition salt using standard techniques.

Some of the tertiary amines which can be produced as described are N-ethyl-7,8-dimethoxycyclopentano[f]-1,2,3,4-tetrahydroisoquinoline, N-propyl-7,8-dimethoxycyclopentano[f]-1,2,3,4-tetrahydroisoquinoline, N-phenylethyl-7,8-diethoxycyclopentano[f]-1,2,3,4-tetrahydroisoquinoline, N-benzyl-7,8-dimethoxycyclopentano[f]-1,2,3,4-tetrahydroisoquinoline, N-(3,4-dimethoxybenzyl)-7,8-dimethoxycyclopentano [f]-1,2,3,4-tetrahydroisoquinoline, N-(3,4,5-trimethoxyphenylethyl)-7,8dimethoxycyclopentano[f]1,2,3,4-tetrahydroisoquinoline, N-(diphenylethyl)-7,8-dimethoxycyclopentano[f]-1,2,3,4-tetrahydroisoquinoline, N-(4-fluorophenylethyl)-7,8-dimethoxycyclopentano[f]-1,2,3,4-tetrahydroisoquinoline and N-(4-methylbenzyl)-7,8-diethoxycyclopentano[f]-1,2,3,4-tetrahydroisoquinoline.

The compounds of Formula 2 in which $R_4$ is methyl can be prepared by reacting the secondary amines previously named above with formic acid and formaldehyde at an elevated temperature according to standard procedures for methylating secondary amines to tertiary amines by this process. Some of the tertiary amines which are produced in this way are N-methyl-7,8-dimethoxycyclopentano[f]-1,2,3,4-tetrahydroisoquinoline, N-methyl-7,8-diethoxycyclopentano[f]-1,2,3,4-tetrahydroisoquinoline and N-methyl-7,8-dipropoxycyclopentano [f]-1,2,3,4-tetrahydroisoquinoline.

A second method of making the compounds of Formula 2 is to react the secondary amine starting materials with an appropriate aldehyde to form an intermediate imine or Schiff's base which can then be reduced catalytically with hydrogen at a moderate pressure and moderately elevated temperature. This process can be represented as follows:

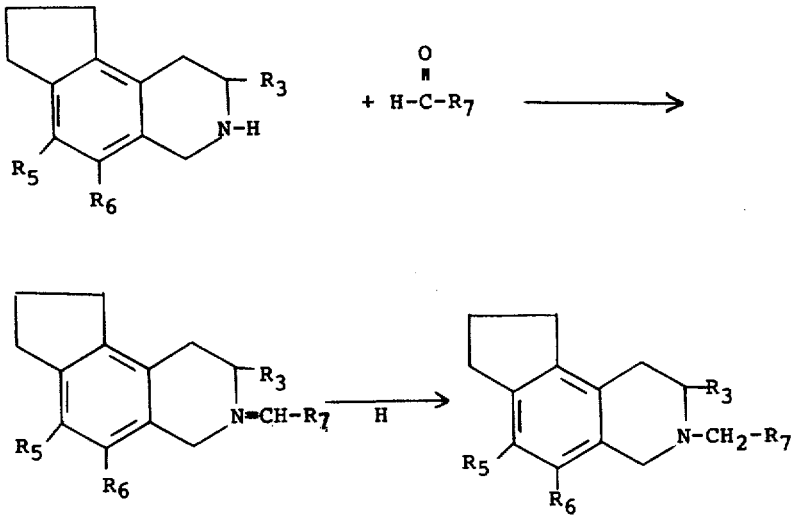

wherein $R_3$, $R_5$, $R_6$ and $R_7$ have the previously assigned significance.

Representative of the aldehydes which can be used in this process are acetaldehyde, propionaldehyde, butyraldehyde, benzaldehyde, 3,4-dimethoxybenzaldehyde, phenylacetaldehyde, diphenylacetaldehyde, p-chlorobenzaldehyde, $\beta,\beta,\beta$-trifluoropropionaldehyde, 3,5-dimethylbenzaldehyde and $\alpha$-phenylpropionaldehyde.

Some of the Schiff's bases or imines which are produced as intermediates in the described process are N-ethylidene-7,8-dimethoxycyclopentano[f]-1,2,3,4-tetrahydroisoquinoline, N-propylidene-7,8-dimethoxycyclopentano[f]-1,2,3,4-tetrahydroisoquinoline, N-benzylidene-7,8-diethoxycyclopentano[f]-1,2,3,4-tetrahydroisoquinoline, N-phenylethylidene-7,8-dipropoxycyclopentano[f]-1,2,3,4-tetrahydroisoquinoline and N-diphenylethylidene-7,8-dimethoxycyclopentano [f]-1,2,3,4-tetrahydroisoquinoline.

Reduction of the intermediate imines can be readily effected by catalytic hydrogenation at moderate pressures using platinium oxide or palladium as the catalyst and a suitable liquid carrier such as glacial acetic acid at room temperature or a moderately elevated temperature, such as up to 50°C. Following completion of the hydrogen uptake the reaction mixture can be handled in a conventional way to isolate the desired tertiary amine. Tertiary amines such as those previously named herein can be produced by this process.

The tertiary amines provided by this invention having 7,8-dialkoxy substituents can be converted to the corresponding 7,8-dihydroxy compounds by use of concentrated hydrogen bromide or hydrogen iodide in water or acetic acid solution to cleave the ether linkages. It is preferred to use 48 percent hydrogen bromide in water for this cleavage. The reaction proceeds readily at an elevated temperature, and preferably the reflux temperature. The process can be represented as follows:

esters by reaction with suitable esterifying agents such as alkanoic acid anhydrides, alkanoyl halides, alkanoic acids and aralkanoyl halides. This process can be represented as follows:

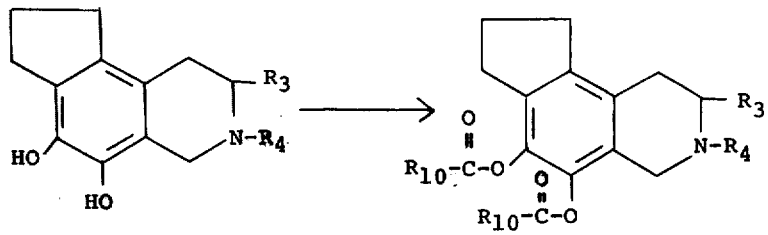

wherein $R_{10}$ is a lower alkyl or aryl-lower alkyl group and $R_3$ and $R_4$ have the previously assigned significance.

Conventional methods can be used to prepare and isolate the esters. Some of the esters which can be produced from the otherwise corresponding 7,8-dihydroxy compounds are N-methyl-7,8-diacetoxycyclopentano[f]-1,2,3,4-tetrahydroisoquinoline, N-propyl-7,8-dipropionyloxycyclopentano[f]-1,2,3,4-tetrahydroisoquinoline, N-benzyl-7,8-dibenzoyloxycyclopentano[f]-1,2,3,4-tetrahydroisoquinoline and N-diphenylethyl-7,8-diphenylacetyloxycyclopentano[f]-1,2,3,4-tetrahydroisoquinoline.

The tertiary amines of this invention can be converted to acid addition salts by contacting the amines with a suitable inorganic acid such as hydrochloric acid, sulfuric acid, phosphoric acid and hydrobromic acid or an organic acid such as citric acid, acetic acid, formic acid, malic acid, fumaric acid, succinic acid, benzoic acid and tartaric acid.

Quaternary ammonium salts of the compounds are readily prepared by contacting the compounds with an alkyl halide or an alkyl sulfate, aralkyl halide or aralkyl

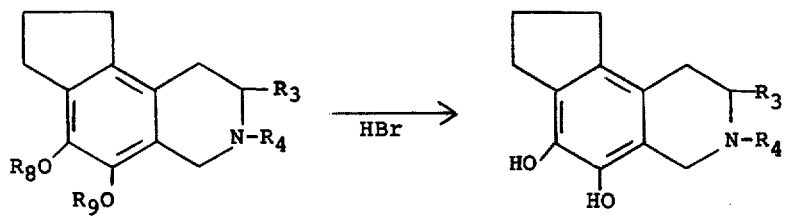

wherein $R_8$ and $R_9$ are lower alkyl groups and $R_3$ and $R_4$ have the previously assigned significance.

Some of the compounds which can be produced by cleavage of the alkoxy groups from the 7,8-positions are N-ethyl-7,8-dihydroxycyclopentano[f]-1,2,3,4-tetrahydroisoquinoline, N-propyl-7,8-dihydroxycyclopentano[f]-1,2,3,4-tetrahydroisoquinoline, N-phenylethyl-7,8-dihydroxycyclopentano[f]-1,2,3,4-tetrahydroisoquinoline, N-benzyl-7,8-dihydroxycyclopentano[f]-1,2,3,4-tetrahydroisoquinoline, N-(3,4-dimethoxybenzyl)-7,8-dihydroxycyclopentano[f]-1,2,3,4-tetrahydroisoquinoline, N-(3,4,5-trimethoxyphenylethyl)-7,8-dihydroxycyclopentano[f]-1,2,3,4-tetrahydroisoquinoline, N-(diphenylethyl)-7,8-dihydroxycyclopentano[f]-1,2,3,4-tetrahydroisoquinoline, N-(4-fluorophenylethyl)-7,8-dihydroxycyclopentano[f]-1,2,3,4-tetrahydroisoquinoline and N-(4-methylbenzyl)-7,8-dihydroxycyclopentano[f]-1,2,3,4-tetrahydroisoquinoline.

The N-substituted -7,8-dihydroxycyclopentano[f]-1,2,3,4-tetrahydroisoquinolines can be converted to sulfate such as methyl chloride, ethyl bromide, propyl iodide, benzyl chloride, benzyl sulfate and methyl sulfate as well as other compounds known to form quaternary ammonium salts with tertiary amines.

The tertiary amines of this invention are useful as neutralizing agents since they are bases which form salts with acids.

According to a second aspect of the invention, the compounds are also useful pharmaceutically. These compounds as the base or acid addition salt when administered to animals parenterally or orally exert an anti-hypertensive effect. The compounds thus can be used to reduce blood pressure.

N-($\beta$-3,4-Dimethoxyphenylethyl)-7,8-dimethoxycyclopentano[f]-1,2,3,4-tetrahydroisoquinoline hydrobromide has an $ALD_{50}$ in mice of 125 to 140 mg/kg i.p. when administered as a suspension in 1 percent tragacanth. When administered at 50 mg/kg i.p. in 1 percent tragacanth to hypertensive rats the following percent change in systolic blood pressure was observed:

| 1 hour   | −26.0 ± 4.3 |
|----------|-------------|
| 2 hours  | −11.3 ± 2.2 |
| 4 hours  | −6.6 ± 4.2  |
| 24 hours | −2.8 ± 2.8  |

N-($\beta,\beta$-diphenylpropionyl)-7,8-dimethoxycyclopentano [f]-1,2,3,4-tetrahydroisoquinoline has an $ALD_{50}$ in mice of 100 to 180 mg/kg i.p. when administered in polyethyleneglycol 400. When administered at 20 mg/kg i.p. in polyethylene glycol 400 to hypertensive rats the following percent change in systolic blood pressure was observed:

| 1 hour   | −4.4 ± 0.9 |
|----------|------------|
| 2 hours  | −6.9 ± 3.0 |
| 4 hours  | −5.0 ± 1.9 |
| 24 hours | −2.1 ± 1.3 |

N-(3,4-dimethoxyphenylacetyl)-7,8-dimethoxycyclopentano[f]-1,2,3,4-tetrahydroisoquinoline as the base has an $ALD_{50}$ of 160–180 mg/kg i.p. when administered to mice in polyethylene glycol 400. When administered at 20 mg/kg i.p. in polyethylene glycol 400 to hypertensive rats the following percent change in systolic blood pressure was observed:

| 1 hour   | −5.4 ± 1.8 |
|----------|------------|
| 2 hours  | −3.9 ± 2.0 |
| 4 hours  | −6.3 ± 1.1 |
| 24 hours | −3.1 ± 1.1 |

N-methyl-7,8-dihydroxycyclopentano[f]-1,2,3,4-tetrahydroisoquinoline as the base in water has an $ALD_{50}$ in mice of 150 to 200 mg/kg i.p. In the anesthetized normotensive dog a dose of 5 mg/kg i.v. of the base in water lowered blood pressure 48 percent and after 18 minutes there was a 50 percent return to normal blood pressure.

N-(2-methylbutyl)-7,8-dimethoxycyclopentano[f]-1,2,3,4-tetrahydroisoquinoline as the base has an $ALD_{50}$ in mice of 100–200 mg/kg i.p. when administered in water. When administered as the base at 20 mg/kg i.p. in water to hypertensive rats the following percent change in systolic blood pressure was observed:

| 1 hour   | −13.1 ± 2.7 |
|----------|-------------|
| 2 hours  | −8.1 ± 2.8  |
| 4 hours  | −7.0 ± 1.2  |
| 24 hours | −1.6 ± 0.8  |

N-(3,4-dimethoxybenzyl)-7,8-dimethoxycyclopentano [f]-1,2,3,4-tetrahydroisoquinoline as the base has an $ALD_{50}$ of 141 to 159 mg/kg i.p. when administered to mice as a suspension in 1 percent tragacanth. When administered at 50 mg/kg i.p. as the base in a suspension in 1 percent tragacanth to hypertensive rats the following percent change in systolic blood pressure was observed:

| 1 hour   | −8.8 ± 2.9 |
|----------|------------|
| 2 hours  | −4.2 ± 3.2 |
| 4 hours  | −0.7 ± 1.7 |
| 24 hours | +0.9 ± 3.3 |

N-(3,3-diphenylpropyl)-7,8-dimethoxycyclopentano[f]-1,2,3,4-tetrahydroisoquinoline has an $ALD_{50}$ in mice greater than 1000 mg/kg i.p. when administered as a suspension in 1 percent tragacanth. When administered at 100 mg/kg i.p. in 1 percent tragacanth to hypertensive rats the following percent change in systolic blood pressure was observed:

| 1 hour   | −3.5 ± 3.5 |
|----------|------------|
| 2 hours  | −7.9 ± 2.7 |
| 4 hours  | −6.7 ± 1.6 |
| 24 hours | −7.0 ± 1.8 |

N-methyl-7,8-dimethoxycyclopentano[f]-1,2,3,4-tetrahydroisoquinoline as the base has an $ALD_{50}$ in mice of 100 to 150 mg/kg i.p. when administered in water. When administered at 50 mg/kg i.p. in water to hypertensive rats the following percent change in systolic blood pressure was observed;

| 1 hour   | −3.0 ± 5.5 |
|----------|------------|
| 2 hours  | −2.9 ± 2.4 |
| 4 hours  | −6.3 ± 2.2 |
| 24 hours | −4.6 ± 2.7 |

N-(3,4-dimethoxybenzoyl)-7,8-dimethoxycyclopentano [f]-1,2,3,4-tetrahydroisoquinoline has an $ALD_{50}$ of 150 to 200 mg/kg i.p. when administered to mice in polyethylene glycol 400. When administered at 20 mg/kg i.p. in polyethylene glycol 400 to hypertensive rats the following percent change in systolic blood pressure was observed:

| 1 hour   | −4.0 ± 3.3 |
|----------|------------|
| 2 hours  | −1.4 ± 3.5 |
| 4 hours  | −3.1 ± 3.2 |
| 24 hours | +5.6 ± 3.8 |

The amount of active ingredient administered may be varied; however, it is necessary that the amount of active ingredient be such that a suitable dosage is given. The selected dosage depends upon the desired therapeutic effect and on the duration of treatment. Dosages of from 0.1 to 25 mg/kg of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg of active agent.

A typical tablet can have the composition:

| | Mg |
|---|---|
| Active agent (1) | 100 |
| Starch U.S.P. | 57 |
| Lactose U.S.P. | 73 |
| Talc. U.S.P. | 9 |
| Stearic acid | 12 |

1. N-(β-3,4-dimethoxyphenylethyl)-7,8-dimethoxycyclopentano [f]-1,2,3,4-tetrahydroisoquinoline hydrobromide.

The compounds exhibit both oral and parenteral activity and accordingly they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art, such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

THE PREPARATION OF STARTING MATERIALS USED IN THIS INVENTION

Intermediate indanaldehydes of the following formula are first prepared:

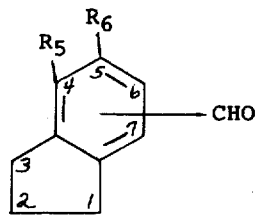

in which the -CHO is in the 6- or 7-position and $R_5$ and $R_6$ have the previously assigned meaning. These compounds are prepared by reducing a 4,5-dialkoxy-1-indanone to 4,5-dialkoxyindane and then converting that compound by means of a Friedel-Crafts reaction to a mixture of 4,5-dialkoxy-6-indanaldehyde and 4,5-dialkoxy-7-indanaldehyde. This series of reactions can be represented as follows:

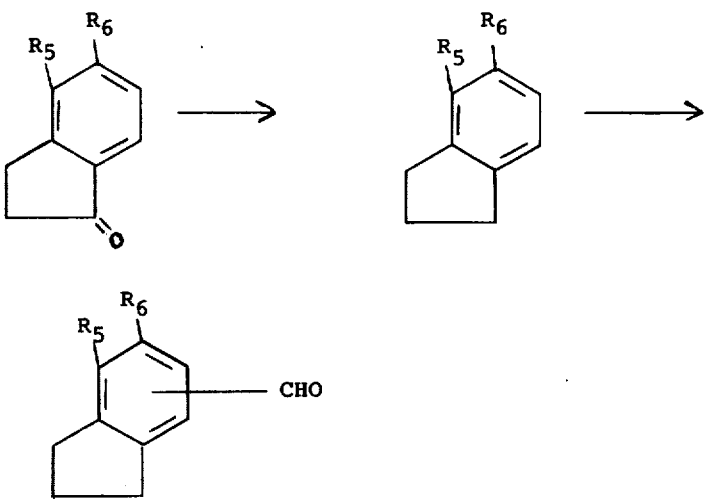

wherein $R_5$ and $R_6$ have the previously assigned significance.

Among the starting materials which can be used in the described sequence of reactions are 4,5-dimethoxy-1-indanone, 4,5-diethoxy-1-indanone, 4,5-dipropoxy-1-indanone and 4-methoxy-5-ethoxy-1-indanone. The publication of John Koo in J. Am. Chem. Soc., 75, 1891 (1953) discloses 4,5-dimethoxy-1-indanone. Other similar compounds, such as those just named, can be prepared by the procedure disclosed therein.

Reduction of the 4,5-dialkoxy-1-indanone can be readily achieved catalytically using hydrogen and a suitable catalyst such as palladium. The hydrogenation is effected by placing the starting material in glacial acetic acid containing the catalyst and a small amount of concentrated hydrochloric acid. The hydrogenation proceeds readily at room temperature using a hydrogen pressure of about 25 to 100 psig. After hydrogen uptake has ceased the product can be recovered from the reaction mixture by conventional methods.

Some 4,5-dialkoxyindanes which can be produced as described are 4,5-dimethoxyindane, 4,5-diethoxyindane, 4,5-dipropoxyindane, 4,5-diisopropoxyindane, 4,5-dibutoxyindane and 4-methoxy-5-ethoxyindane.

Formylation of a 4,5-dialkoxyindane according to the method of Alfred Rieche et al. in Chem. Ber., 93, 88 (1960) using a Friedel-Crafts catalyst such as stannic tetrachloride, aluminum trichloride or titanium tetrachloride and α,α-dichloromethyl methyl ether followed by water leads to the production of a mixture containing 4,5-dialkoxy-6-indanaldehyde and 4,5-dialkoxy-7-indanaldehyde. The presence of a mixture of isomeric aldehydes is shown by gas-liquid chromatography. A mixture of 4,5-dimethoxy-6- and -7-indanaldehydes formed by the described procedure contains about 75 percent of the 7-formyl and 25 percent of the 6-formyl isomers. Obviously, the presence of other alkoxy groups than the methoxy group could lead to different amounts of the isomers in the resulting mixture.

The isomeric mixture of aldehydes obtained by the described process is generally a liquid. Residual amounts of solvent are removed from the liquid by distillation following which the product is distilled under high vacuum to give a pure liquid mixture. Upon cooling, one of the isomeric aldehydes crystallizes from the liquid and is removed by filtration. Thus, 4,5-dimethoxy-7-indanaldehyde crystallizes and leaves a liquid which is primarily 4,5-dimethoxy-6-indanaldehyde. Fractional distillation of the liquid gives the pure 6-formyl isomer.

Some of the separated purified aldehydes which can be prepared by the described method are:

4,5-dimethoxy-7-indanaldehyde,
4,5-diethoxy-7-indanaldehyde,
4,5-dipropoxy-7-indanaldehyde,
4,5-dibutoxy-7-indanaldehyde, and 4-methoxy-5-ethoxy-7-indanaldehyde.

The 7,8-dialkoxycyclopentano[f]-1,2,3,4-tetrahydroisoquinolines of Formula 3 are prepared from the 4,5-dialkoxy-7-indanaldehydes by reacting the aldehyde with a 1-nitroalkane to produce a 4,5-dialkoxy-7-nitrovinylindane, chemically reducing the nitrovinyl compound to the corresponding aminoalkyl compound, reacting the resulting amine with formaldehyde to produce a Schiff's base and then treating the Schiff's base with acid to effect a Pictet-Spengler acid catalyzed ring closure. This series of reactions can be represented as follows:

with the nitroalkane can be readily effected by procedures discussed in Gairaud et al., J. Org. Chem. 18, 1 (1953) and particularly by the use of ammonium acetate in glacial acetic acid at an elevated temperature.

By following the described procedure there is obtained 4,5-dimethoxy-7-nitrovinylindane, 4,5-dimethoxy-7-(2-nitro-2-methylvinyl)indane, 4,5-dimethoxy-7-(2-nitro-2-ethylvinyl)indane, 4,5-diethoxy-7-nitrovinylindane, 4,5-dipropoxy-7-nitrovinylindane and 4-methoxy-5-ethoxy-7-nitrovinylindane.

The 4,5-dialkoxy-7-nitrovinylindanes are readily reduced chemically by means of lithium aluminum hydride in dry ether according to the method of Marchant et al., J. Chem. Soc. 327 (1956) to produce the desired 4,5l-dialkoxy-7-aminoethylindanes. Some of the compounds which are produced in this way are 4,5-dimethoxy-7-aminoethylindane, 4,5-diethoxy-7-(2-aminopropyl)indane, 4,5-dipropoxy-7-(2-aminobutyl)indane and 4-methoxy-5-ethoxy-7-aminoethylindane.

The 4,5-dialkoxy-7-aminoethylindanes are converted to the Schiff's bases by reaction with formaldehyde using conventional reaction conditions for preparing Schiff's bases. Some of the compounds so produced are N-methylidene-4,5-dimethoxy-7-(2-aminoethyl)indane, N-methylidene-4,5-diethoxy-7(2-aminopropyl)indane, N-methylidene-4,5-dipropoxy-7-(2-aminobutyl)indane and N-methylidene-4-methoxy-5-ethoxy-7-(2-aminoethyl)indane.

The described Schiff's bases are readily cyclized in aqueous acid, such as 23 percent hydrochloric acid, at a moderately elevated temperature of about 40° to 75° C., to the cyclopentano[f]-1,2,3,4-tetrahydroisoquino-

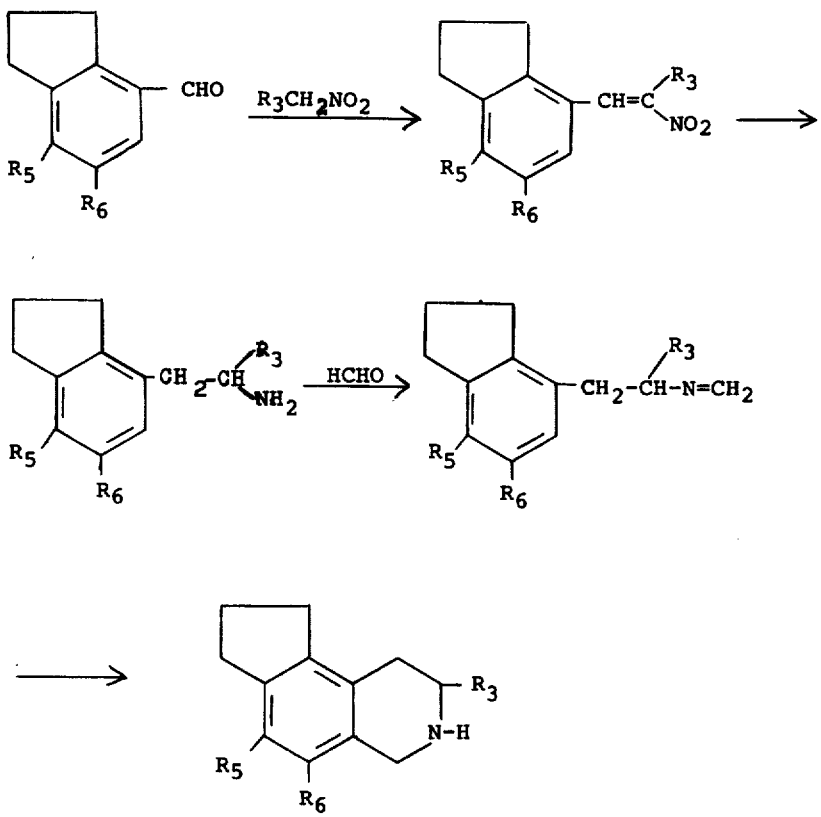

wherein $R_3$, $R_5$ and $R_6$ have the previously assigned significance.

In effecting the first step of this series of reactions, nitromethane, nitroethane, 1-nitropropane and other such 1-nitroalkanes can be used.

Condensation of the 4,5-dialkoxy-7-indanaldehyde lines. The product is readily recovered by evaporation of the solvent and acid.

Representative cyclopentano[f]-1,2,3,4-tetrahydroisoquinolines which are produced as described are 7,8-dimethoxycyclopentano[f]-1,2,3,4-tetrahydroisoquinoline, 7,8-diethoxycyclopentano[f]-1,2,3,4- tetrahydroisoquinoline, 7,8-dipropoxycyclopentano[f]-1,2,3,4-tetrahydroisoquinoline and 7-methoxy-8-ethoxy-cyclopentano[f]-1,2,3,4-tetrahydroisoquinoline.

The following examples are presented to illustrate the invention.

EXAMPLE 1

N-(2-Methylbutyl)-7,8-dimethoxycyclopentano[f]-1,2,3,4-tetrahydroisoquinoline hydrobromide To 4.5 g (0.052 mole) of 2-methylbutryaldehyde refluxing in 150 ml of benzene was added slowly 4.06 g (0.017 mole) of 7,8-dimethoxycyclopentano[f]-1,2,3,4-tetrahydroisoquinoline in 125 ml of benzene. After refluxing into a Dean-Stark trap and removing 0.2 ml of water, the solvent was removed on an evaporator, the dark red oil remaining was dissolved in 55 ml of glacial acetic acid and hydrogenated at 45 psi over 0.5 g of $PtO_2$. The catalyst was removed by filtration through a filter aid, washed with methanol and the acid neutralized with 60 g of sodium hydroxide in water. The product was extracted with ether while salting out with sodium chloride until no color was given with Dragendorf's reagent. Thorough removal of the ether gave 4.98 g of cherry red oil which was dissolved in anhydrous isopropyl ether and precipitated by addition of hydrogen chloride gas. The resulting sticky solid was filtered and dried in a vacuum oven, giving a brown mass of gummy solid which did not crystallize from acetonitrile but came out as an oil when ether was added. The solvent was removed and an attempt to crystallize from ethanol:ethyl acetate was unsuccessful. Most of the solvent was removed and the remaining material was dissolved in water. Some black impurity was filtered, and the solution was made basic and extracted with ether. The ether was removed giving a dark red oil which was distilled under high vacuum giving a cherry red liquid (2.02 g). This oil was dissolved in benzene and hydrogen bromide gas was added; no precipitate occurred. The solvent was removed and the yellow oil was dried overnight which hardened it considerably. This was stirred under anhydrous ether with a stirring bar several times giving a powder. This powder was successfully recrystallized from ethylacetate yielding 1.17 g (15.8 percent) of the hydrobromide salt, m.p. 139.5°–142°C.

Anal. Calcd. for $C_{19}H_{30}BrNO_2$:
C, 59.37; H, 7.86;
N, 3.64; Br, 20.78.
Found:
C, 59.17; H, 7.80;
N, 3.56; Br, 20.98.

EXAMPLE 2

N-Methyl-7,8-dimethoxycyclopentano[f]-1,2,3,4-tetrahydroisoquinoline hydrobromide After refluxing 2.45 g (0.0105 mole) of 7,8-dimethoxycyclopentano[f]-1,2,3,4-tetrahydroisoquinoline in 8.12 ml of 88 percent formic acid and 4.96 ml of formalin for 6 hrs., the acid solution was washed into a separatory funnel and neutralized with concentrated ammonium hydroxide. The precipitate was extracted with ether and the ether was distilled giving a cherry red oil. The hydrobromide salt of the oil yielded a solid, after drying, which recrystallized well from ethylacetate:absolute ethanol. Two recrystallizations gave a pure sample, m.p. 228.5–230°C., 1.42 g (41%).

Anal. Calcd. for $C_{15}H_{22}BrNO_2$:
C, 54.88; H, 6.75;
N, 4.26; Br, 24.34.
Found:
C, 55.08; H, 6.74;
N, 4.13; Br, 24.41.

EXAMPLE 3

N-($\beta,\beta$-Diphenylpropionyl)-7,8-dimethoxycyclopentano[f]-1,2,3,4-tetrahydroisoquinoline $\beta,\beta$-Diphenylpropionyl chloride was prepared by refluxing 2.45 g (0.016 mole) of the corresponding acid with a large excess of $SOCl_2$ in benzene. After removing the $SOCl_2$, the resulting acid chloride and 2.45 g (0.0105 mole) of 7,8-dimethoxycyclopentano[f]-1,2,3,4-tetrahydroisoquinoline and 4.0 ml of triethylamine were refluxed 7–8 hrs. The reaction mixture was cooled, rinsed into a separatory funnel and washed with 150 ml of water, 2 × 100 ml of 15 percent sulfuric acid, 2 × 100 ml of 10 percent sodium hydroxide, and 2 × 100 ml of water. The benzene solution was dried over anhydrous sodium sulfate and then the solvent was thoroughly removed on an evaporator giving a highly viscous oil which was further dried in a vacuum oven. The oil did not solidify and all attempts to recrystallize it failed. Column chromatography on silica gel gave a pure material. The adsorbent was packed down dry before passing benzene through. The compound was added as a solution in benzene and eluted as follows: 5 × 100 ml benzene, 2 × 100 ml 75:25 benzene:chloroform, 2 × 100 ml 50:50 benzene: chloroform, 2 × 100 ml 25:75 benzene:chloroform. The amide began eluting in the second 100 ml of 25:75 benzene:chloroform. Very small quantities of oil came out in earlier fractions but were discarded. Elution was continued with 800 ml of 25:75 benzene:chloroform of which the first 600 ml contained most of the amide. Removal of the solvent and thorough drying gave an analytical sample, 1.81 g (27%).

Anal. Calcd. for $C_{29}H_{31}NO_3$: C, 78.88; H, 7.07; N, 3.17.
Found: C, 78.65; H, 7.10; N, 3.10.

EXAMPLE 4

N-(3,3-Diphenylpropyl)-7,8-dimethoxycyclopentano[f]-1,2,3,4-tetrahydroisoquinoline To a slurry of 2.0 g (0.053 mole) of $LiAlH_4$ in 100 ml of dry ether was added 2.96 g (0.0067 mole) of N-($\beta,\beta$-diphenylpropionyl)-7,8-dimethoxycyclopentano[f]-1,2,3,4-tetrahydroisoquinoline in 100 ml of ether. After refluxing about 20 hrs., adding 5.0 g of filter aid and decomposing excess hydride with 15 ml of water, the white precipitate was filtered after the ether solution was decanted several times and the precipitate washed with ether. The ether was thoroughly removed by distillation. Recrystallization twice from methanol gave prisms, 1.64 g (54 percent), m.p. 105°–106.5° C.

Anal. Calcd. for $C_{29}H_{33}NO_2$: C, 81.46; H, 7.77; N, 3.27.
Found: C, 81.55; H, 7.77; N, 3.35.

EXAMPLE 5

N-(2,2-Diphenylethyl)-7,8-dimethoxycyclopentano[f]-1,2,3,4-tetrahydroisoquinoline In 150 ml of benzene, 2.12 g (0.009 mole) of 7,8-dimethoxycyclopentano[f]-1,2,3,4-tetrahydroisoquinoline and 3.0 g (0.015 mole) of diphenylacetaldehyde were refluxed overnight with removal of water in a Dean-Stark trap. After removal of the solvent on a rotary evaporator, the remaining red oil was dissolved in 75 ml of glacial acetic acid and hydrogenated over 0.6 g of $PtO_2$ at 45 psi. The catalyst was removed by filtration and the solvent by rotary evaporation. The resulting oil was treated with dilute hydrochloric acid which left a residue. The solution was made basic with sodium hydroxide, an oily precipitate was extracted with ether, the ether was dried over sodium sulfate and removed by distillation giving 3.11 g of an orange-red oil. This oil was dissolved in benzene and reacted with hydrogen bromide gas to give a hard glassy solid upon removal of the benzene but which did not crystallize after many attempts. The material was dissolved in acetonitrile:ethylacetate, the volume was reduced on a steam bath and on cooling a black tarry precipitate occurred. The solvent was removed and the free base was extracted after treating the residue with NaOH. The darkly colored glass obtained was chromatographed on silica gel under the same conditions as in Example 3. A light colored oil was obtained (in the 25:75 benzene:chloroform fractions) which crystallized from methanol giving 1.07 g of prisms (28%) m.p. 100°–102°C.

Anal. Calcd. for $C_{28}H_{31}NO_2$: C, 81.32; H, 7.55; H, 3.38.

Found: C, 81.34; H, 7.37; N, 3.20.

EXAMPLE 6

N-(3,4-Dimethoxyphenylacetyl)-7,8-dimethoxycyclopentano[f]-1,2,3,4-tetrahydroisoquinoline In 75 ml of benzene and 5–6 ml of triethylamine, 2.45 g (0.0105 mole) of 7,8-dimethoxycyclopentano[f]-1,2,3,4-tetrahydroisoquinoline and 2.36 g (0.011 mole) of 3,4-dimethoxyphenylacetyl chloride were refluxed overnight. The reaction solution was cooled, washed with 150 ml of water, 2 × 100 ml of 10 percent sulfuric acid, 2 × 100 ml of 10 percent sodium hydroxide and finally 150 ml of water. The solvent was removed on a rotary evaporator yielding 4.08 g of a viscous oil which resisted attempts at recrystallization. The oil was purified by column chromatography similar to the procedure described in Example 3. The oil came off in the 25:75 benzene:chloroform fractions giving 1.688 g (39 percent).

Anal. Calcd. for $C_{24}H_{29}NO_5$: C, 70.05; H, 7.10; N, 3.40.

Found: C, 69.77; H, 7.13; N, 3.11.

EXAMPLE 7

N-(β-3,4-Dimethoxyphenylethyl)-7,8-dimethoxycyclopentano[f]-1,2,3,4-tetrahydroisoquinoline hydrobromide To 0.5 g (0.013 mole) of $LiAlH_4$ in anhydrous ether was added dropwise 1.27 g (0.0034 mole) of N-(3,4-dimethoxyphenylacetyl)-7,8-dimethoxycyclopentano[f]-1,2,3,4-tetrahydroisoquinoline in ether. After refluxing 24 hrs., 1.5 g of filter aid was added and excess $LiAlH_4$ was decomposed with cooling and very slow addition of water (dropwise). The white precipitate was washed with ether followed by decantation several times and then the precipitate was filtered. Removal of the ether on a rotary evaporator gave 1.22 g of light pink oil. The free amine did not crystallize from methanol, methanol-ether or methanol-water. The hydrobromide salt was obtained by bubbling hydrogen bromide gas through an ether solution of the amine. After filtering and drying the precipitate it was recrystallized several times from acetonitrile giving 1.05 g (71 percent) of white solid, m.p. 234°–236°C.

Anal. Calcd. for $C_{24}H_{32}NO_4Br$:
C, 60.25; H, 6.74;
N, 2.92; Br, 16.70.
Found:
C, 60.00; H, 6.65;
N, 2.78; Br, 16.60.

EXAMPLE 8

N-(3,4-Dimethoxybenzoyl)-7,8-dimethoxycyclopentano[f]-1,2,3,4-tetrahydroisoquinoline The acid chloride of 3,4-dimethoxybenzoic acid was prepared by the general method described in Example 3 from 2.0 g (0.011 mole) of the acid. After refluxing 2.30 g (0.010 mole) of 7,8-dimethoxycyclopentano[f]-1,2,3,4-tetrahydroisoquinoline with the acid chloride and 6 ml of triethylamine in 250 ml of benzene overnight, the reaction mixture was cooled and washed with 2 × 150 ml of water, 2 × 100 ml of 10 percent (V/V) sulfuric acid, 2 × 100 ml of 10 percent sodium hydroxide and finally 2 × 100 ml of water. Removal of the solvent gave 4.15 g of an amber oil which possessed a very intense amide carbonyl absorption in the infrared. This compound was purified by chromatographing twice on silica gel as described in Example 3. By this method 1.12 g (29 percent) of very viscous oil was obtained.

Anal. Calcd. for $C_{23}H_{27}NO_5$: C, 69.50; H, 6.84; N, 3.52.

Found: C, 69.34; H, 6.78; N, 3.40.

EXAMPLE 9

N-(3,4-Dimethoxybenzyl)-7,8-dimethoxycyclopentano[f]-1,2,3,4-tetrahydroisoquinoline hydrochloride To 0.8 g (0.021 mole) of $LiAlH_4$ in 100 ml of anhydrous ether was added 2.25 g (0.0057 mole) of N-(3,4-dimethoxybenzoyl)-7,8-dimethoxycyclopentano[f]-1,2,3,4-tetrahydroisoquinoline dropwise in 100 ml of ether. After refluxing overnight, 3.0 g of filter aid was added followed by dropwise addition of 5–6 ml of water. Ether was decanted and the white precipitate was washed with ether several times followed by decantation and finally filtration. Distillation of the solvent and drying in an oven yielded 1.85 g of an oil which showed absence of the carbonyl amide absorption in the infrared. The hydrochloride salt of the amine was obtained by adding slowly an ether solution of anhydrous hydrogen chloride to a solution of the amine in anhydrous ether. The salt was washed well with dry ether, filtered and further dried giving 2.01 g of material which recrystallized well from acetonitrile giving 1.36 g (57 percent), m.p. 222.5°–224°C.

Anal. Calcd. for $C_{23}H_{20}NO_4Cl$:
C, 65.78; H, 7.20;
N, 3.33; Cl, 8.44.
Found:
C, 65.88; H, 7.15;
N, 3.43; Cl, 8.56.

EXAMPLE 10

N-Methyl-7,8-dihydroxycyclopentano[f]-1,2,3,4-tetrahydroisoquinoline hydrobromide After refluxing 2.0 g (0.0061 mole) of N-methyl-7,8-dimethoxycyclopentano[f]-1,2,3,4-tetrahydroisoquinoline hydrobromide for 2 hrs. under nitrogen in 25 ml of 48 percent HBr, the solution was evaporated to dryness on a rotary evaporator. Drying was completed in a vacuum oven at about 60° C. Excess acetonitrile was necesary to dissolve the product. Upon reducing the volume by approximately two-thirds crystallization occurred. Recrystallization from acetonitrile and decolorizing with activated charcoal gave 0.775 g (43%), m.p. 242°–244° C.

Anal. Calcd. for $C_{13}H_{18}NO_2Br$:
C, 52.01; H, 6.04;
N, 4.66; Br, 26.61.
Found:
C, 52.14; H, 5.96;
N, 4.72; Br, 26.67.

EXAMPLE 11

N-Methyl-7,8-diacetoxycyclopentano[f]-1,2,3,4-tetrahydroisoquinoline trifluoroacetate To 1.0 g (0.0033 mole) of N-methyl-7,8-dihydroxycyclopentano[f]-1,2,3,4-tetrahydroisoquinoline hydrobromide in 5.0 g (0.083 mole) of glacial acetic acid was added 18 g of trifluoroacetic anhydride. Heat was evolved when the anhydride was added accompanied by dissolution of the amine. After stirring 0.5 hr. and refluxing overnight, hydrogen bromide gas was bubbled through the reaction solution for 1 minute and then the volatile components were removed on a rotary evaporator. The resulting oil was further dried in a vacuum oven at 60°–70° C. in the presence of fresh $P_2O_5$ for several days. The remaining viscous material was stirred with a glass rod in anhydrous ether until it began to solidify and form small crystals. Recrystallization was successful from ethanol-ether solution. Several recrystallizations from this solvent system and a decolorization with activated charcoal in absolute ethanol gave 0.59 g (42%), m.p. 169.5°–172°C.

Anal. Calcd. for $C_{19}H_{22}NO_6F_3$:
C, 54.67; H, 5.31;
N, 3.34; F, 13.65.
Found:
C, 55.07; H, 5.49;
N, 3.48; F, 13.40.

The Following Examples are Presented to Illustrate the Preparation of Compounds Used as Starting Materials in the Invention.

EXAMPLE 12

4,5-Dimethoxyindane

A mixture of 52.6 g (0.275 mole) of 4,5-dimethoxy-1-indanone, 3.00 g of 5 percent Pd/C, 100 ml of glacial acetic acid and 20 drops of conc. HCl was hydrogenated at 45 psi and room temperature until hydrogen uptake ceased. Following filtration of the used catalyst, two methods were used to work up the reaction mixture.

A. The acid was neutralized with dilute sodium hydroxide and the product extracted from the aqueous phase with ether. The ether was removed by distillation and crude 4,5-dimethoxyindane was distilled under reduced pressure, b.p. 133°–135° C (15 mm) yielding 42.0 g (86.4 percent) of clear liquid. Infrared analysis showed the absence of carbonyl absorption.

B. Most of the acetic acid was removed on the rotary evaporator and the remaining liquid was distilled as before giving 4,5-dimethoxyindane with no significant difference in yield from that obtained in A.

EXAMPLE 13

4,5-Dimethoxy-7-indanaldehyde

To a solution of 10.0 g (0.056 mole) of 4,5-dimethoxyindane, 24.0 g (0.126 mole) of titanium tetrachloride and 104 ml of $CH_2Cl_2$ in a 250 ml 3-necked flask fitted with a thermometer and condenser and magnetically stirred, 11.0 g (0.096 mole) of α,α-dichloromethyl methyl ether was added rapidly dropwise at 0° C. Hydrogen chloride gas was liberated during the course of the reaction. After vigorous evolution of HCl had subsided, the reaction solution was allowed to slowly warm to room temperature and it was stirred for 1 to 2 hours. The solution was refluxed for 6 hours, cooled and the reaction mixture was poured over 200 ml of ice and water (ether and salt were added at this point to increase the volume of the organic phase, to invert the two layers and to break emulsions). The organic phase was washed with 2 × 100 ml of 8 percent $NaHCO_3$ solution, 1 × 100 ml of water and dried over $Na_2SO_4$. After removal of the solvent by distillation, the mixture of aldehyde isomers was distilled under high vacuum (b.p. 115°–126°C; 0.28 mm) giving 10.2 g of the 6- and 7-position aldehydes (88 percent). The 7-position aldehyde which crystallized from the liquid was filtered. This process was repeated several times by seeding the filtrate followed by cooling. Gas chromatography showed the white crystalline solid 4,5-dimethoxy-7-indanaldehyde to be one component of the two component mixture. In this way 4.24 g of white solid was obtained, m.p. 41°–44° C., yield 38.5 percent.

Anal. Calcd. for $C_{12}H_{14}O_3$: C, 69.88; H, 6.84.
Found: C, 70.03; H, 6.66.

EXAMPLE 14

4,5-Dimethoxy-7-nitrovinylindane

To a 100 ml 3-necked round bottom flask fitted with a condenser and thermometer and magnetically stirred, was added 12.97 g (0.063 mole) of 4,5-dimethoxy-7-indanaldehyde, 3.00 g (0.039 mole) of ammonium acetate, 13.0 ml (0.292 mole) of $CH_3NO_2$ and 40 ml of glacial acetic acid. This mixture was heated for 1 to 2 hours at 112° C. As the reaction solution began to cool the entire solution solidified. After cooling in an ice bath and removing the solvent by filtration, the solid 4,5-dimethoxy-7-nitrovinylindane was washed with a small volume of acetic acid giving fine yellow needles (9.55 g) after thorough drying. The filtrate was poured into 300 ml of ice and water from which precipitated a slightly gummy, yellow-brown solid. This gave an additional 1.43 g of crystalline solid after drying and crystallizing from methanol giving a total yield of 10.98 g (70 percent). An analytical sample melted at 128°–130° C.

Anal. Calcd. for $C_{13}H_{15}NO_4$: C, 62.64; H, 6.06; N, 5.62.
Found: C, 62.79; H, 6.12; N, 5.53.

EXAMPLE 15

4,5-Dimethoxy-7-aminoethylindane

To a slurry of 15.0 g (0.395 mole) of $LiAlH_4$ and 500 ml of anhydrous ether in a 5 liter, 3-necked flask fitted with a condenser, mechanical stirrer and dropping funnel was added 20.0 g (0.084 mole) of 4,5-dimethoxy-7-nitrovinylindane dissolved in 2 liters of ether. The addition was made over a period of about 4 hours while refluxing the ether slurry. When the addition was completed, refluxing was continued for an additional 1 to 2 hours. After the addition of 20 g of diatomaceous earth and then 70 ml of water slowly, dropwise, with cooling in an ice bath, the supernatant ether was decanted, the salts were washed with fresh ether several times followed by decantation and finally filtration. The solvent was removed by distillation and more thoroughly on a rotary evaporator. Cooling in an ice bath gave 15.91 g (90 percent) of 4,5-dimethoxy-7-aminoethylindane as a slightly yellow solid, m.p., 45°–48°C. High vacuum distillation gave an analytical sample.

Anal. Calcd. for $C_{13}H_{19}NO_2$: C, 70.55; H, 8.65; N, 6.32.

Found: C, 70.22; H, 8.49; N, 6.18.

EXAMPLE 16

7,8-Dimethoxycyclopentano[f]-1,2,3,4-tetrahydroisoquinoline hydrochloride

To 11.1 ml of formalin in a round bottom flask heated at 60°–70° C. and magnetically stirred was added 10.95 g (0.049 mole) of 4,5-dimethoxy-7-aminoethylindane (dissolved in 22 ml of methanol) rapidly dropwise. After heating 50 min., the solvent was thoroughly removed on a rotary evaporator. The ir spectrum showed absence of primary amine stretching vibrations at 3190, 3300, 3370 with a weakening in intensity of the peak at 1605 cm$^{-1}$. The N-methylidene-4,5-dimethoxy-7-(2-aminoethyl)indane was dissolved in 55 ml of 23 percent HCl and heated on a water bath with stirring at 50°–60° C. for 30 minutes. The water-acid solvent was removed on the evaporator and the residue was dried overnight in a vacuum oven giving a hard solid which yielded 11.14 g (84.1%) of 7,8-dimethoxycyclopentano[f]-1,2,3,4-tetrahydroisoquinoline when crystallized from acetonitrileabsolute alcohol, m.p. 232°–235°C. dec.

Anal. Calcd. for $C_{14}H_{20}NO_2Cl$:
C, 62.33; H, 7.47;
N, 5.19; Cl, 13.14.
Found:
C, 62.58; H, 7.36;
N, 5.33; Cl, 13.29.

The foregoing detailed description has been given for clearness of understanding only, and no unnecessary limitations should be understood therefrom, as modifications will be obvious to those skilled in the art.

What is claimed is:

1. A compound of the formula

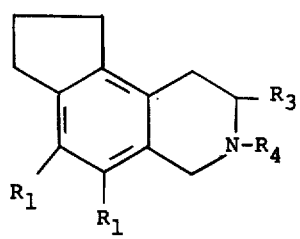

wherein $R_1$ represents hydroxy, alkoxy groups having 1 to 8 carbon atoms or alkanoyloxy groups having 1 to 8 carbon atoms, $R_3$ represents hydrogen or an alkyl group having 1 to 8 carbon atoms, and $R_4$ represents an alkyl group, phenyl-carbonyl, 3,4-dimethoxybenzoyl, phenyl-alkyl, β-3,4-dimethoxyphenylethyl, 3,4-dimethoxybenzyl, benzhydryl-alkyl, alkanoyl, phenyl-alkanoyl, 3,4-dimethoxyphenylacetyl or benzhydrylalkanoyl groups in which groups represented by $R_4$ the alkyl and alkanoyl groups have 1 to 8 carbon atoms, and nontoxic acid addition salts thereof.

2. A compound of the formula

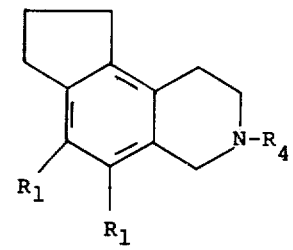

wherein $R_1$ represents hydroxy, alkoxy groups having 1 to 8 carbon atoms or alkanoyloxy groups having 1 to 8 carbon atoms, and $R_4$ represents an alkyl group, phenyl-carbonyl, 3,4-dimethoxybenzoyl, phenyl-alkyl, β-3,4-dimethoxyphenylethyl, 3,4-dimethoxybenzyl, benzhydryl-alkyl, alkanoyl, phenyl-alkanoyl, 3,4-dimethoxyphenylacetyl or benzhydrylalkanoyl groups in which groups represented by $R_4$ the alkyl and alkanoyl groups have 1 to 8 carbon atoms, and nontoxic acid addition salts thereof.

3. A compound according to claim 1 in which $R_1$ and $R_2$ are each the same alkoxy group, $R_3$ is hydrogen and $R_4$ is an alkyl group.

4. A compound according to claim 1 in which $R_1$ and $R_2$ are each the same alkoxy group, $R_3$ is hydrogen and $R_4$ is a phenylalkyl group.

5. A compound according to claim 1 in which $R_1$ and $R_2$ are each the same alkoxy group, $R_3$ is hydrogen and $R_4$ is a benzhydryl-alkyl group.

6. A compound according to claim 1 in which $R_1$ and $R_2$ are each the same alkoxy group, $R_3$ is hydrogen and $R_4$ is an alkanoyl group.

7. A compound according to claim 1 in which $R_1$ and $R_2$ are each the same alkoxy group, $R_3$ is hydrogen and $R_4$ is a benzhydryl-alkanoyl group.

8. A compound according to claim 1 in which $R_1$ and $R_2$ are each the same alkoxy group, $R_3$ is hydrogen and $R_4$ is a benzoyl group.

9. A compound according to claim 1 in which $R_1$ and $R_2$ are each hydroxy, $R_3$ is hydrogen and $R_4$ is an alkyl group.

10. A compound according to claim 1 in which $R_1$ and $R_2$ are each an alkanoyloxy group, $R_3$ is hydrogen and $R_4$ is an alkyl group.

11. A compound according to claim 3 named N-(2-methylbutyl)-7,8-dimethoxycyclopentano[f]-1,2,3,4-tetrahydroisoquinoline.

12. A compound according to claim 3 named N-methyl-7,8-dimethoxycyclopentano[f]-1,2,3,4-tetrahydroisoquinoline.

13. A compound according to claim 7 named N-(β,β-diphenylpropionyl)-7,8-dimethoxycyclopentano[f]-1,2,3,4-tetrahydroisoquinoline.

14. A compound according to claim 5 named N-(3,3-diphenylpropyl)-7,8-dimethoxycyclopentano[f]-1,2,3,4-tetrahydroisoquinoline.

15. A compound according to claim 5 named N-(2,2-diphenylethyl)-7,8-dimethoxycyclopentano[f]-1,2,3,4-tetrahydroisoquinoline.

16. A compound according to claim 1 in which $R_1$ and $R_2$ are each the same alkoxy group, $R_3$ is hydrogen and $R_4$ is a phenylalkanoyl group.

17. A compound according to claim 16 named N-(3,4-dimethoxyphenylacetyl)-7,8-dimethoxycyclopentano[f]-1,2,3,4-tetrahydroisoquinoline.

18. A compound according to claim 1 in which $R_1$ and $R_2$ are each the same alkoxy group, $R_3$ is hydrogen and $R_4$ is benzoyl.

19. A compound according to claim 18 named N-(3,4-dimethoxybenzoyl)-7,8-dimethoxycyclopentano[f]-1,2,3,4-tetrahydroisoquinoline.

20. A compound according to claim 4 named N-(3,4-dimethoxybenzyl)-7,8-dimethoxycyclopentano[f]-1,2,3,4-tetrahydroisoquinoline.

21. A compound according to claim 9 named N-methyl-7,8-dihydroxycyclopentano[f]-1,2,3,4-tetrahydroisoquinoline.

22. A compound according to claim 10 named N-methyl-7,8-diacetoxycyclopentano[f]-1,2,3,4-tetrahydroisoquinoline.

* * * * *